United States Patent [19]

Shoesmith

[11] Patent Number: Plant 5,936

[45] Date of Patent: Apr. 7, 1987

[54] CHRYSANTHEMUM PLANT NAMED PANTHER

[75] Inventor: May V. Shoesmith, Westfield, England

[73] Assignee: Ball Pan Am Plant Company, Parrish, Fla.

[21] Appl. No.: 746,856

[22] Filed: Jun. 20, 1985

[51] Int. Cl.[4] ..... A01H 5/00

[52] U.S. Cl. ..... Plt./78

[58] Field of Search ..... Plt./78

*Primary Examiner*—James R. Feyrer

*Attorney, Agent, or Firm*—Schwartz, Jeffery, Schwaab, Mack, Blumenthal & Evans

[57] ABSTRACT

A Chrysanthemum plant named Panther having globular cushion capitulum form and button flower type, bright yellow color, diameter across face of flower of 0.75" to 1.5", uniform eight week flowering response when grown photoperiodically, and natural outdoor flowering date of October 8 in the midwest and October 31 in Florida, and by its height of 6" to 8" when grown photoperiodically and 1' to 2' when grown outdoors.

1 Drawing Figure

1

The present invention comprises a new and distinct cultivar of *Chrysanthemum morifolium,* Ramat., hereinafter referred to by the cultivar name Panther.

Panther is a product of a planned breeding program which had the objective of creating new garden Chrysanthemum cultivars with compact cushion habit, yellow button flowers, and with the ability to be grown year around in 4" pots. Such traits in combination were not present or needed improvement in previously available commercial cultivars.

Panther was originated from a hybridization made by May Victoria Shoesmith in a controlled breeding program in Westfield, Woking, England in 1977. The male and female parents are unknown at this time.

Panther was discovered and selected as one flowering plant within the progeny of the stated parentage by or under the supervision of May Victoria Shoesmith in November of 1978 in a controlled environment in West Chicago, Ill., and given the code #FG-78-377-YS.

The first act of asexual reproduction of Panther was accomplished when vegetative cuttings were taken from the initial selection in February of 1979 in a controled environment in West Chicago, Ill. by a technician working under formulations established and supervised by May Victoria Shoesmith. Horticultural examination of selected units initiated February of 1979 has demonstrated that the combination of characteristics as herein disclosed for Panther are firmly fixed and are retained through successive generations of asexual reproduction.

Panther has not been observed under all possible environmental conditions. The phenotype may vary significantly with variations in enviornment such as temperature, light intensity and day length. The following observations, measurements and comparisons describe plants grown in West Chicago, Ill. under greenhouse and field conditions which approximate those generally used in commercial practice.

The following traits have been repeatedly observed and are determined to be basic characteristics of Panther which in combination distinguish this chrysanthemum as a new and distinct cultivar:

(1) Globular cushion capitulum form.

(2) Button flower type.

(3) Bright yellow color.

(4) Diameter across face of the flower 0.75" to 1.5".

2

(5) Uniform 8 week flowering response using photoperiodic control. Natural outdoor flowering date is October 8 in the midwest and October 31 in Florida.

(6) Height when plant is grown photoperiodically is 6" to 8" above the edge of a 4" pot, with height depending on the number of long days prior to bud initiation, maturity of the cutting and the temperature. In the garden, plant will attain a height of 1' to 2'.

Of the many commercial cultivars known to the present inventor, the most similar in comparison to Panther is Bruin. In comparison to Bruin, Panther has a slightly darker flower color, a smaller flower, and a more compact cushion habit. The flower form and plant performance are similar to those same characteristics of Bruin.

The accompanying photographic drawing shows typical inflorescence and foliage characteristics of Panther. The photograph is in black and white except for a cluster of flowers which represent the true flower color of Panther.

In the following description, color references are made to The Royal Horticultural Society Colour Chart. The color values were determined at approximately 12:00 noon on May 2, 1985 under inflorescent light at Bradenton, Fla.

Classification:

*Botanical.*—*Chrysanthemum morifolium,* Ramat., cv Panther.

*Commercial.*—Garden and greenhouse mum.

INFLORESCENCE

A. Capitulum:

*Form.*—Globular cushion.

*Type.*—Button.

*Diameter across face.*—0.50" to 1.5".

B. Corolla of ray florets:

*Color (general tonality from a distance of three meters).*—Yellow gold.

*Color (upper surface).*—6A, center 154A, greenish yellow.

*Color (under surface).*—6A.

C. Corolla of disc florets:

*Color (mature).*—Yellow.

*Color (immature).*—154A, greenish yellow.

D. Reproductive organs:

*Androecium.*—Present in disc florets only; insignificant.

*Gynoecium.*—One per both ray and disc floret.

PLANT

A. General appearance:

*Height.*—1′ to 2′ when grown outside in natural season conditions; 6″ above edge of 4″ pot under normal greenhouse conditions.

B. Foliage:

*Color (upper surface).*—147A.

*Color (under surface).*—147B.

*Shape.*—Deeply lobed, margin repand.

I claim:

1. A new and distinct cultivar of Chrysanthemum plant named Panther, as described and illustrated, and particularly characterized by its globular cushion capitulum form and button flower type, bright yellow color, diameter across face of flower of 0.75″ to 1.5″, uniform eight week flowering response when grown photoperiodically, and natural outdoor flowering date of October 8 in the midwest and October 31 in Florida, and by its height of 6″ to 8″ when grown photoperiodically and 1′ to 2′ when grown outdoors.

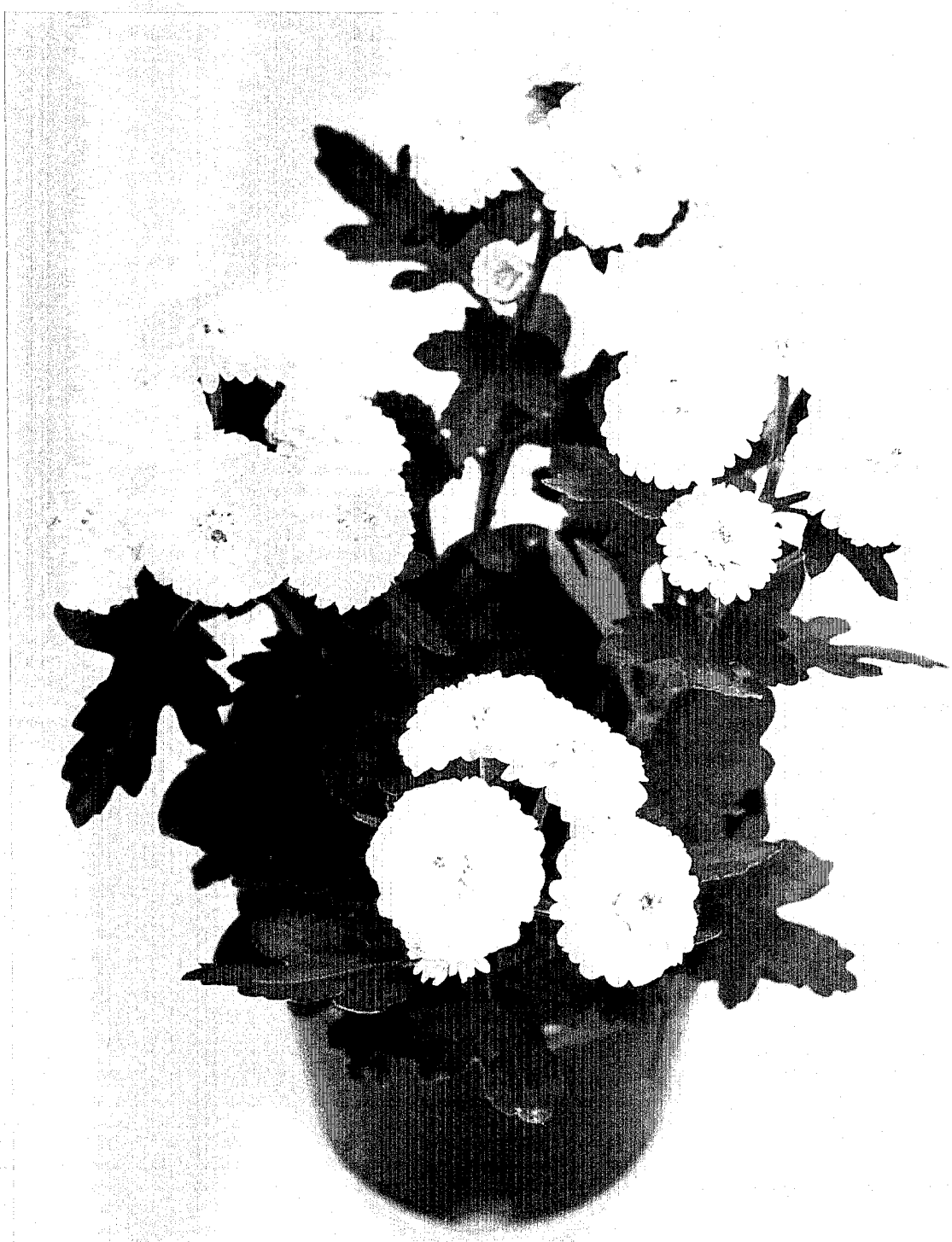

* * * * *